(12) United States Patent
Johnson

(10) Patent No.: US 11,825,924 B2
(45) Date of Patent: Nov. 28, 2023

(54) SMOKER'S HYGIENE ASSEMBLY

(71) Applicant: Constance Johnson, Aubrey, TX (US)

(72) Inventor: Constance Johnson, Aubrey, TX (US)

( * ) Notice: Subject to any disclaimer, the term of this patent is extended or adjusted under 35 U.S.C. 154(b) by 596 days.

(21) Appl. No.: 16/929,315

(22) Filed: Jul. 15, 2020

(65) Prior Publication Data

US 2022/0015514 A1    Jan. 20, 2022

(51) Int. Cl.
*A45C 5/00* (2006.01)
*A61K 8/04* (2006.01)
*B65D 83/04* (2006.01)
*A45C 13/02* (2006.01)
*A61Q 15/00* (2006.01)

(52) U.S. Cl.
CPC .............. *A45C 5/005* (2013.01); *A45C 13/02* (2013.01); *A61K 8/046* (2013.01); *A61Q 15/00* (2013.01); *B65D 83/0409* (2013.01)

(58) Field of Classification Search
CPC ........ A45C 5/005; A45C 13/02; A61Q 15/00; A61K 8/046
USPC ......................................................... 206/581
See application file for complete search history.

(56) References Cited

U.S. PATENT DOCUMENTS

| | | | | |
|---|---|---|---|---|
| 2,038,319 A | * | 4/1936 | Stanley | A45C 11/008 206/823 |
| 2,167,926 A | * | 8/1939 | Glasker | A45C 11/008 206/581 |
| 2,209,781 A | * | 7/1940 | Lewis | A45C 13/02 206/581 |
| 2,219,597 A | * | 10/1940 | Lutz | A45D 29/20 132/73 |
| 2,353,932 A | * | 7/1944 | Schaffer | A45C 11/008 132/312 |
| 3,187,757 A | | 6/1965 | Jones, Jr. | |
| D280,864 S | | 10/1985 | Allen | |
| 4,979,525 A | * | 12/1990 | Chiou | A46B 7/04 132/289 |
| 5,025,928 A | * | 6/1991 | Orosy | A45D 27/22 206/581 |
| 5,095,924 A | * | 3/1992 | Stanfield | A45D 44/18 206/581 |
| D341,487 S | * | 11/1993 | Glos, II | D3/284 |
| 6,016,916 A | * | 1/2000 | Ortner | B05B 11/0038 206/823 |
| 6,206,192 B1 | * | 3/2001 | Winstead | A61C 19/02 206/572 |
| 6,834,655 B1 | * | 12/2004 | Briscoe | A45D 42/10 132/288 |
| 8,789,541 B1 | * | 7/2014 | Evans | B65D 81/113 132/73 |

(Continued)

FOREIGN PATENT DOCUMENTS

WO    WO2004037036    6/2004

*Primary Examiner* — Ernesto A Grano

(57) ABSTRACT

A smoker's hygiene assembly for performing smoker's hygiene includes a case that has a plurality of storage wells integrated therein. A bottle of body spray is provided and the bottle of body spray is stored in a respective one of the storage slots. A bottle of hand cream is provided and the hand cream is stored in a respective one of the storage slots. A bottle of hand sanitizer is provided and the bottle of hand sanitizer is stored in a respective one of the storage slots. A tin of breath mints is provided and the tin of breath mints is stored in a respective one of the storage wells.

5 Claims, 3 Drawing Sheets

(56) References Cited

U.S. PATENT DOCUMENTS

| | | | | | |
|---|---|---|---|---|---|
| 8,851,089 | B1* | 10/2014 | Rogers | A45C 11/26 132/312 |
| 10,617,577 | B2* | 4/2020 | Templeton | A61F 17/00 |
| 2003/0209462 | A1* | 11/2003 | Godshaw | A45C 7/0054 190/102 |
| 2004/0222125 | A1* | 11/2004 | Meing | A45C 11/26 206/581 |
| 2006/0110701 | A1* | 5/2006 | Cwik | A61B 1/0669 433/29 |
| 2006/0186145 | A1* | 8/2006 | Rager | B65D 1/0261 222/534 |
| 2006/0289030 | A1* | 12/2006 | Pho | A46B 15/0091 132/309 |
| 2007/0000941 | A1* | 1/2007 | Hadden | A47K 5/1217 222/63 |
| 2007/0108091 | A1* | 5/2007 | Stewart | A61L 9/14 206/581 |
| 2008/0302699 | A1* | 12/2008 | Berg | B65D 83/04 206/581 |
| 2008/0317697 | A1 | 12/2008 | Sturgis | |
| 2009/0044827 | A1* | 2/2009 | Zilber | A45D 40/24 132/297 |
| 2009/0149361 | A1 | 6/2009 | Adkison | |
| 2011/0308992 | A1* | 12/2011 | Bahcall | B65D 75/566 206/812 |
| 2012/0138507 | A1* | 6/2012 | Recchia | B65D 83/04 206/581 |
| 2013/0240617 | A1* | 9/2013 | Ramsey | G06F 16/58 235/375 |
| 2015/0004560 | A1* | 1/2015 | Arnold | A61Q 11/00 424/53 |
| 2015/0037270 | A1 | 2/2015 | Pressly | |
| 2015/0083755 | A1* | 3/2015 | Mecker | B65D 83/201 222/183 |
| 2015/0208788 | A1 | 7/2015 | Dass | |
| 2015/0265019 | A1* | 9/2015 | Niedzwiecki | A45C 13/005 220/509 |
| 2021/0267332 | A1* | 9/2021 | Gies | A47C 7/386 |
| 2022/0079818 | A1* | 3/2022 | Calvert | A61F 13/20 |
| 2022/0097944 | A1* | 3/2022 | Roberts | A45F 5/021 |

\* cited by examiner

SMOKER'S HYGIENE ASSEMBLY

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to hygiene devices and more particularly pertains to a new hygiene device for performing smoker's hygiene.

(2) Description of Related Art Including Information Disclosed Under 37 CFR 1.97 and 1.98

The prior art relates to hygiene devices including a toiletry kit comprising a cylindrical carrying case and a plurality of dispensing bottles each being stored in the cylindrical carrying case. The prior art discloses a shaving kit that includes a proprietary skin moisturizer and a proprietary body lotion. The prior art discloses a personal cleansing kit that includes a heated cream, an aromatic compound and a musical recording. The prior art discloses a skin care kit that includes a proprietary blend of skin moisturizing lotions. The prior art discloses a travel case that carries travel sized toiletries, including bath soap, a razor, a toothbrush, toothpaste, shampoo and a towel. The prior art discloses a toiletry bag that includes a zippered opening.

BRIEF SUMMARY OF THE INVENTION

An embodiment of the disclosure meets the needs presented above by generally comprising a case that has a plurality of storage wells integrated therein. A bottle of body spray is provided and the bottle of body spray is stored in a respective one of the storage slots. A bottle of hand cream is provided and the hand cream is stored in a respective one of the storage slots. A bottle of hand sanitizer is provided and the bottle of hand sanitizer is stored in a respective one of the storage slots. A tin of breath mints is provided and the tin of breath mints is stored in a respective one of the storage wells.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
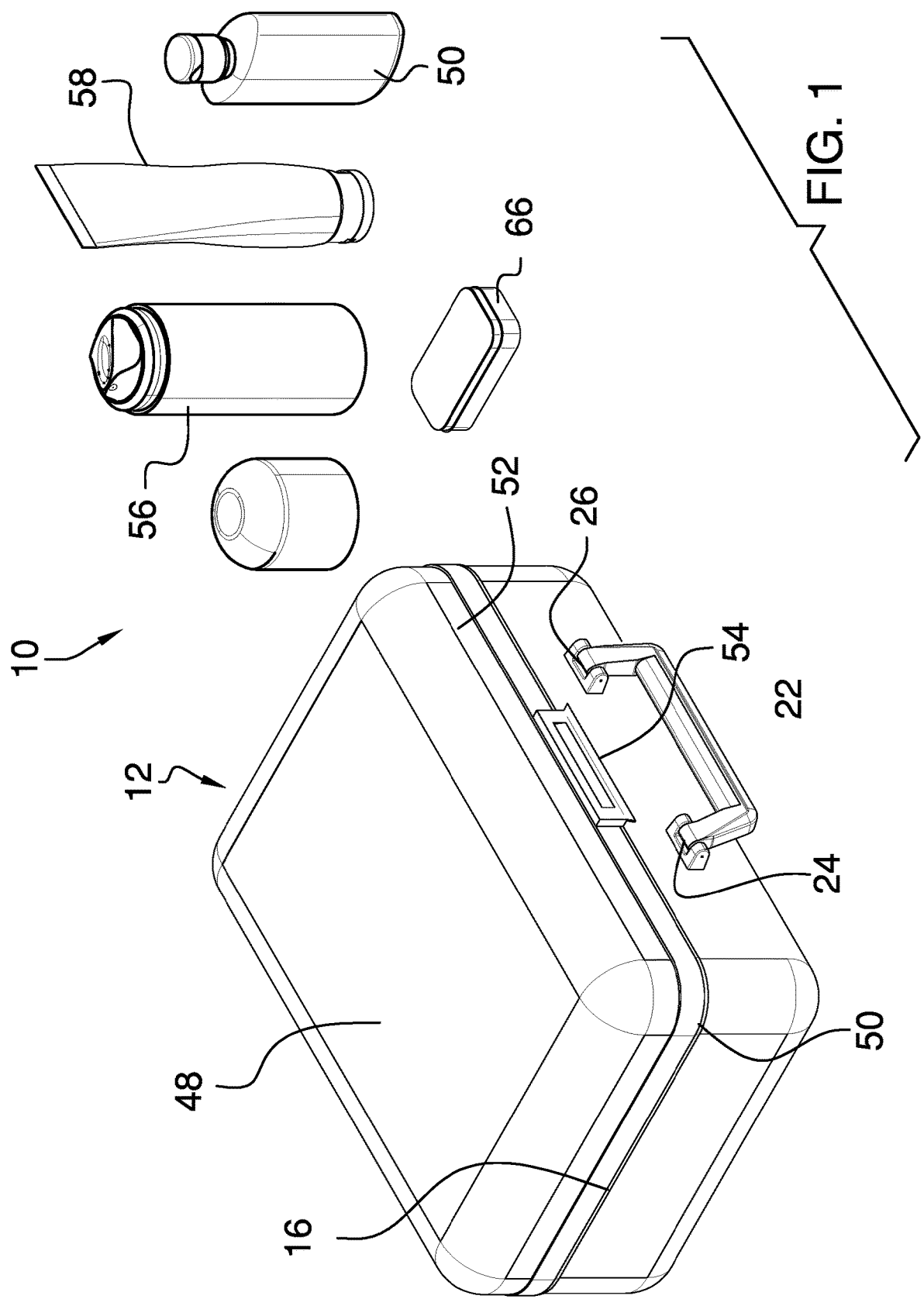
FIG. 1 is a perspective view of a smoker's hygiene assembly according to an embodiment of the disclosure.
Figure 2:
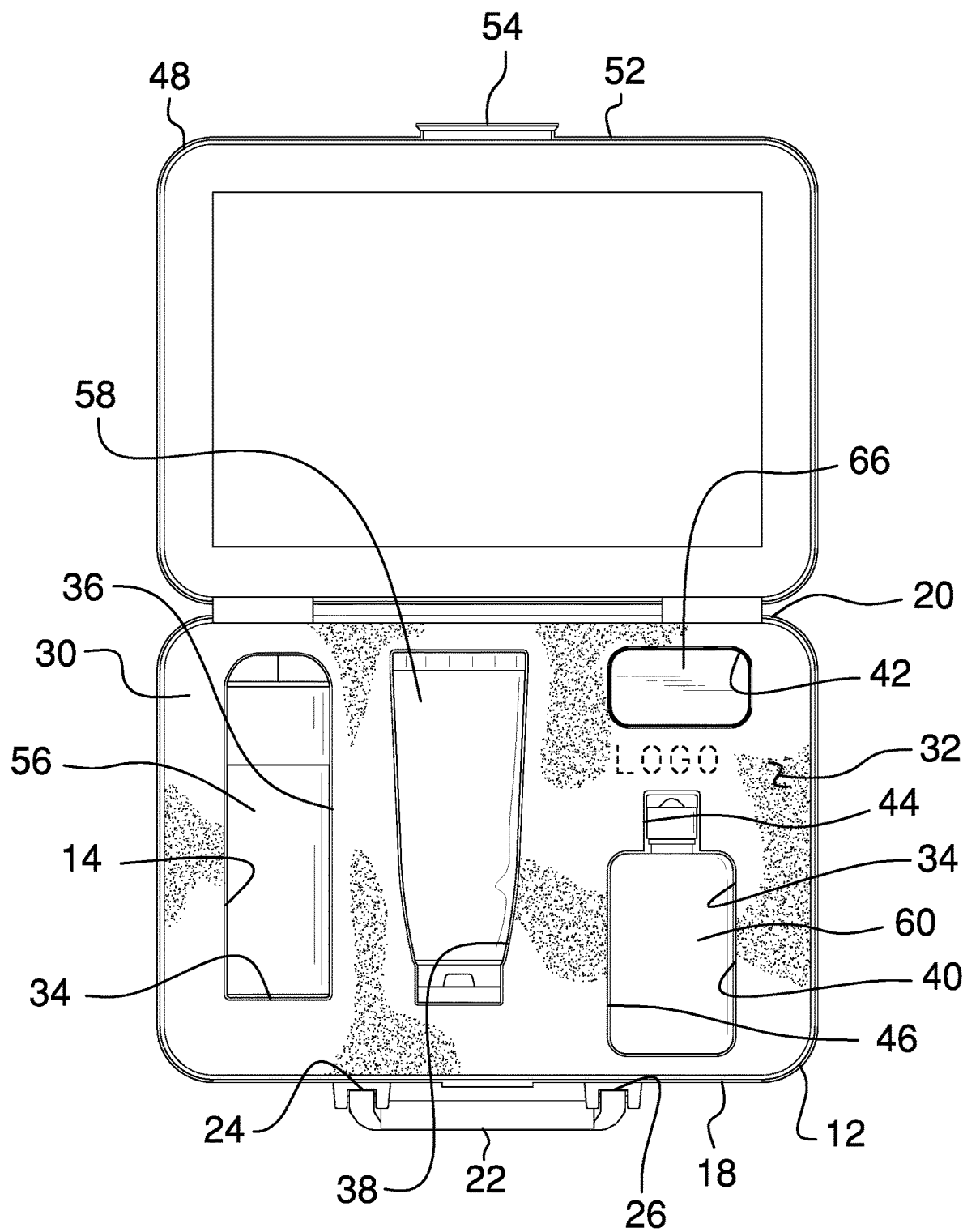
FIG. 2 is a top view of an embodiment of the disclosure.
Figure 3:
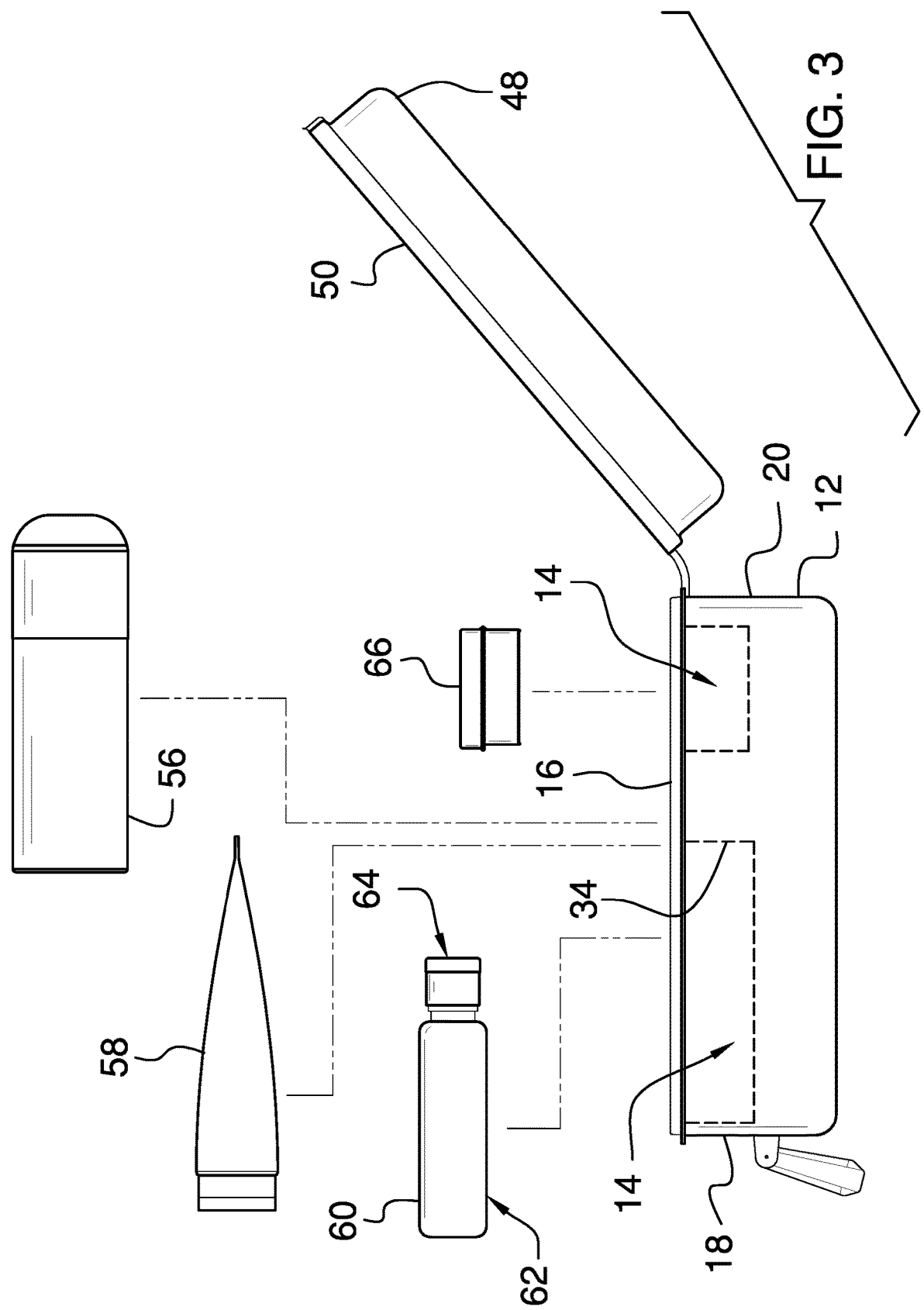
FIG. 3 is an exploded perspective view of an embodiment of the disclosure.

With reference now to the drawings, and in particular to FIGS. 1 through 3 thereof, a new hygiene device embodying the principles and concepts of an embodiment of the disclosure and generally designated by the reference numeral 10 will be described.

As best illustrated in FIGS. 1 through 3, the smoker's hygiene assembly 10 generally comprises a case 12 that has a plurality of storage wells 14 integrated therein. The case 12 has a top edge 16, a front wall 18 and a back wall 20. A handle 22 is pivotally coupled to the front wall 18 of the case 12 for carrying the case 12. The handle 22 has a first end 24 and a second end 26, the handle 22 is curved between the first end 24 and the second end 26, and each of the first end 24 and the second end 26 is pivotally attached to the front wall 18. Additionally, an engagement 28 is coupled to the front wall 18 of the case 12.

An insert 30 is positioned in the case 12 and the insert 30 has a top surface 32. Additionally, the top surface 32 is aligned with the top edge 16 of the case 12. Each of the storage wells 14 extends downwardly through the top surface 32 and the storage wells 14 are spaced apart from each other and are distributed over the top surface 32. Each of the storage wells 14 has a bounding surface 34 and the bounding surface 34 of each of the storage wells 14 defines a unique shape with respect to each of the storage wells 14.

The plurality of storage wells 14 includes a body spray well 36, a hand cream well 38, a hand sanitizer well 40 and a mint tin well 42. Each of the body spray well 36 and the hand cream well 38 is longitudinally elongated, and the mint tin well 42 has a rectangular shape. The hand sanitizer well 40 has a first section 44 that has a lesser width than a second section 46. The insert 30 may be comprised of a resiliently compressible material, such as foamed rubber or other similar type of material.

A lid 48 is hingedly coupled to the case 12 for opening and closing the case 12. The lid 48 has a bottom edge 50 and a forward wall 52, and the bottom edge 50 is hingedly coupled to the top edge 16 of the case 12 along the back wall 20 of the case 12. The bottom edge 50 abuts the top edge 16 of the case 12 when the lid 48 is closed. A closure 54 is provided and the closure 54 is coupled to the forward wall 52 of the lid 48. The closure 54 releasably engages the engagement 28 on the front wall 18 of the case 12 for retaining the lid 48 in a closed position.

A bottle of body spray 56 is provided for spraying body spray on a user. The body spray comprises an aerosol deodorant specifically designed to conceal odors associated with smoking. In this way the body spray can facilitate the user to eliminate bodily odors that are commonly associated with smoking tobacco, marijuana or other popular combustible inhalants. The bottle of body spray 56 is stored in a respective one of the storage wells 14, specifically the body spray well 36.

A bottle of hand cream 58 is provided for applying hand cream on the user. The hand cream comprises a hydrating skin treatment to soothe skin irritation caused by smoking. The hand cream is stored in a respective one of the storage wells 14, specifically the hand cream well 38. A bottle of hand sanitizer 60 is provided for applying hand sanitizer on the user's hands. The hand sanitizer comprises a viscous anti-bacterial compound to kill bacteria on the user's hands.

The bottle of hand sanitizer 60 is stored in a respective one of the storage wells 14. Moreover, the bottle of hand sanitizer 60 comprises a reservoir 62 and a dispenser 64 that is coupled to the reservoir 62. The dispenser 64 is positionable in the first section 44 of the hand sanitizer well 40 and the reservoir 62 is positionable in the second section 46 of the hand sanitizer well 40. A tin of breath mints 66 is provided for freshening the user's breath. The breath mints are infused with a chemical breath freshener to conceal breath odors associated with smoking. Additionally, the tin of breath mints 66 is stored in a respective one of the storage wells 14, specifically the mint well 42.

In use, the user carries the case 12 with them whenever the user is smoking. In this way the bottle of body spray 56, the bottle of hand cream 58, the bottle of hand sanitizer 60 and the tin of breath mints 66 are available while the user is smoking. Thus, the user can conceal bodily odors and breath odors that are associated with smoking. Additionally, the user can keep their hands moisturized and sanitized during and after smoking. In this way the user can perform personal hygiene for eliminating odors and relieving bodily discomfort associated with smoking.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A smoker's hygiene assembly for facilitating a smoker to perform bodily hygiene after smoking, said assembly comprising:
    a case having a plurality of storage wells integrated therein;
    a lid being hingedly coupled to said case for opening and closing said case;
    a bottle of body spray for spraying body spray on a user, said body spray comprising an aerosol deodorant wherein said body spray is configured to conceal odors associated with smoking, said bottle of body spray being stored in a respective one of said storage wells;
    a bottle of hand cream for applying hand cream on the user, said hand cream comprising a hydrating skin treatment wherein said hand cream is configured to soothe skin irritation caused by smoking, said hand cream being stored in a respective one of said storage wells;
    a bottle of hand sanitizer for applying hand sanitizer on the user's hands, said hand sanitizer comprising a viscous anti-bacterial compound wherein said hand sanitizer is configured to kill bacteria on the user's hands, said bottle of hand sanitizer being stored in a respective one of said storage wells;
    a tin of breath mints for freshening the user's breath, said breath mints being infused with a chemical breath freshener wherein said breath mints are configured to conceal breath odors associated with smoking, said tin of breath mints being stored in a respective one of said storage wells;
    wherein said case has a top edge, a front wall and a back wall;
    wherein said assembly includes a handle being pivotally coupled to said front wall of said case for carrying said case, said handle having a first end and a second end, said handle being curved between said first end and said second end, each of said first end and said second end being pivotally attached to said front wall;
    wherein said assembly includes an engagement being coupled to said front wall of said case; and
    an insert being positioned in said case, said insert having a top surface, said top surface being aligned with a top edge of said case, each of said storage wens extending downwardly through said top surface, said storage wells being spaced apart from each other and being distributed over said top surface, each of said storage wells having a bounding surface said bounding surface of each of said storage wells defining a unique shape with respect to each of said storage wells.

2. The assembly according to claim 1, wherein said plurality of storage wells includes a body spray well, a hand cream well, a hand sanitizer well and a mint tin well, each of said body spray well and said hand cream well being longitudinally elongated, said mint tin well having a rectangular shape, said hand sanitizer well having a first section having a lesser width than a second section.

3. The assembly according to claim 2, wherein:
    said bottle of body spray is positionable in said body spray well;
    said hand cream is positionable in said hand cream well;

said bottle of hand sanitizer comprises a reservoir and a dispenser being coupled to said reservoir, said dispenser being positionable in said first section of said hand sanitizer well, said reservoir being positionable in said second section of said hand sanitizer well; and said tin of breath mints being positionable in said breath mint well.

4. The assembly according to claim 1, wherein:

said lid has a bottom edge and a forward wall, said bottom edge being hingedly coupled to said top edge of said case along said back wall of said case, said bottom edge abutting said top edge of said case when said lid is closed; and said assembly includes a closure being coupled to said forward wall of said lid, said closure releasably engaging said engagement on said front wall of said case for retaining said lid in a closed position.

5. A smoker's hygiene assembly for facilitating a smoker to perform bodily hygiene after smoking, said assembly comprising:

a case having a plurality of storage wells integrated therein, said case having a top edge, a front wall and a back wall;

a handle being pivotally coupled to said front wall of said case for carrying said case, said handle having a first end and a second end, said handle being curved between said first end and said second end, each of said first end and said second end being pivotally attached to said front wall;

an engagement being coupled to said front wall of said case;

an insert being positioned in said case, said insert having a top surface, said top surface being aligned with said top edge of said case, each of said storage wells extending downwardly through said top surface, said storage wells being spaced apart from each other and being distributed over said top surface, each of said storage wells having a bounding surface, said bounding surface of each of said storage welts defining a unique shape with respect to each of said storage wells, said plurality of storage wells including a body spray well, a hand cream well, a hand sanitizer well and a mint tin well, each of said body spray well and said hand cream well being longitudinally elongated, said mint tin well having a rectangular shape, said hand sanitizer well having a first section having a lesser width than a second section;

a lid being hingedly coupled to said case for opening and closing said case, said lid having a bottom edge and a forward wall, said bottom edge being hingedly coupled to said top edge of said case along said back wall of said case, said bottom edge abutting said top edge of said case when said lid is closed;

a closure being coupled to said forward wall of said lid, said closure releasably engaging said engagement on said front wall of said case for retaining said lid in a closed position;

a bottle of body spray for spraying body spray on a user, said body spray comprising an aerosol deodorant wherein said body spray is configured to conceal odors associated with smoking, said bottle of body spray being stored in a respective one of said storage wells, said bottle of body spray being positionable in said body spray well;

a bottle of hand cream for applying hand cream on the user, said hand cream comprising a hydrating skin treatment wherein said hand cream is configured to soothe skin irritation caused by smoking, said hand cream being stored in a respective one of said storage wells, said hand cream being positionable in said hand cream well;

a bottle of hand sanitizer for applying hand sanitizer on the user's hands, said hand sanitizer comprising a viscous anti-bacterial compound wherein said hand sanitizer is configured to kill bacteria on the user's hands, said bottle of hand sanitizer being stored in a respective one of said storage wells, said bottle of hand sanitizer comprising a reservoir and a dispenser being coupled to said reservoir, said dispenser being positionable in said first section of said hand sanitizer well, said reservoir being positionable in said second section of said hand sanitizer well; and a tin of breath mints for freshening the user's breath, said breath mints being infused with a chemical breath freshener wherein said breath mints are configured to conceal breath odors associated with smoking, said tin of breath mints being stored in a respective one of said storage wells, said tin of breath mints being positionable in said breath mint well.

* * * * *